(12) United States Patent
Liu et al.

(10) Patent No.: US 11,033,759 B2
(45) Date of Patent: Jun. 15, 2021

(54) RADIOTHERAPY DEVICE AND SYSTEM

(71) Applicant: SHENZHEN OUR NEW MEDICAL TECHNOLOGIES DEVELOPMENT CO., LTD., Guangdong (CN)

(72) Inventors: Haifeng Liu, Guangdong (CN); Peng Zan, Guangdong (CN)

(73) Assignee: SHENZHEN OUR NEW MEDICAL TECHNOLOGIES DEVELOPMENT CO., LTD., Guangdong (CN)

( * ) Notice: Subject to any disclaimer, the term of this patent is extended or adjusted under 35 U.S.C. 154(b) by 319 days.

(21) Appl. No.: 16/090,615

(22) PCT Filed: Sep. 15, 2017

(86) PCT No.: PCT/CN2017/101841
§ 371 (c)(1),
(2) Date: Oct. 2, 2018

(87) PCT Pub. No.: WO2019/051756
PCT Pub. Date: Mar. 21, 2019

(65) Prior Publication Data
US 2020/0376301 A1  Dec. 3, 2020

(51) Int. Cl.
*A61N 5/10* (2006.01)

(52) U.S. Cl.
CPC ......... *A61N 5/1081* (2013.01); *A61N 5/1042* (2013.01); *A61N 5/1065* (2013.01); *A61N 2005/1092* (2013.01)

(58) Field of Classification Search
CPC .. A61N 5/1081; A61N 5/1065; A61N 5/1042; A61N 2005/1092
See application file for complete search history.

(56) References Cited

U.S. PATENT DOCUMENTS 6,031,888 A * 2/2000 Ivan .................... A61B 6/4441
378/196
6,670,614 B1 * 12/2003 Plut ...................... G01T 1/1648
250/363.01
(Continued)

FOREIGN PATENT DOCUMENTS

| CN | 105920745 A | 9/2016 |
| CN | 106714905 A | 5/2017 |

(Continued)

*Primary Examiner* — Marcus H Taningco
(74) *Attorney, Agent, or Firm* — Daniel J. Chalker; Edwin S. Flores; Chalker Flores, LLP (57) ABSTRACT

Provided are a radiotherapy device and system. The device includes: a fixed machine frame, a rotary machine frame, an imaging device and a treatment couch disposed on a side of the fixed machine frame. The treatment couch can move away from or close to the fixed machine frame along a first direction. The rotary machine frame is rotatably connected to the fixed machine frame provided with a treatment source; and the imaging device includes a ray emitter and a detector which are disposed oppositely, the ray emitter and/or the detector are/is disposed on the fixed machine frame, and rays emitted by the ray emitter are received by the detector after passing the affected part of patient, for capturing images of the affected part of the patient. The imaging device and the radiotherapy device are integrally designed, thereby effectively improving the locating accuracy of radiotherapy device, and improving effects of radiotherapy.

20 Claims, 3 Drawing Sheets

(56) References Cited

U.S. PATENT DOCUMENTS

| | | | | |
|---|---|---|---|---|
| 7,298,821 | B2* | 11/2007 | Ein-Gal | A61B 6/4441 |
| | | | | 378/205 |
| 10,456,599 | B2* | 10/2019 | Jordan | A61B 6/4014 |
| 2004/0184579 | A1* | 9/2004 | Mihara | A61B 6/548 |
| | | | | 378/65 |
| 2006/0113482 | A1* | 6/2006 | Pelizzari | A61N 5/1065 |
| | | | | 250/370.09 |
| 2007/0230660 | A1* | 10/2007 | Herrmann | A61N 5/1082 |
| | | | | 378/65 |
| 2008/0219407 | A1* | 9/2008 | Kaiser | A61N 5/10 |
| | | | | 378/65 |
| 2009/0003523 | A1* | 1/2009 | Raanes | A61B 6/4458 |
| | | | | 378/65 |
| 2009/0065717 | A1* | 3/2009 | Kaiser | A61N 5/1049 |
| | | | | 250/505.1 |
| 2009/0097614 | A1* | 4/2009 | Bergfjord | A61N 5/10 |
| | | | | 378/65 |
| 2010/0027744 | A1* | 2/2010 | Brown | A61N 5/1084 |
| | | | | 378/65 |
| 2010/0322381 | A1 | 12/2010 | Stahl et al. | |
| 2012/0307973 | A1* | 12/2012 | Dirauf | A61B 6/4014 |
| | | | | 378/62 |
| 2014/0046601 | A1* | 2/2014 | Carlsson | G06F 19/3481 |
| | | | | 702/19 |
| 2015/0190658 | A1* | 7/2015 | Yu | A61N 5/10 |
| | | | | 600/1 |
| 2017/0189724 | A1* | 7/2017 | Liu | A61N 5/1049 |
| 2018/0192978 | A1* | 7/2018 | Naylor | G21K 1/025 |
| 2019/0069856 | A1* | 3/2019 | Achkire | A61N 5/1042 |

FOREIGN PATENT DOCUMENTS

| | | |
|---|---|---|
| CN | 106924887 A | 7/2017 |
| CN | 206424436 U | 8/2017 |

* cited by examiner

RADIOTHERAPY DEVICE AND SYSTEM

CROSS-REFERENCE TO RELATED APPLICATIONS

This application is a U.S. National Stage Application of and claims priority to International Application No. PCT/CN2017/101841, filed on Sep. 15, 2017, the contents of which are incorporated by reference herein in their entirety.

TECHNICAL FIELD

The present disclosure relates to a radiotherapy device and a system.

BACKGROUND

A radiotherapy device generally includes a machine frame and a treatment couch. The machine frame is annular or C-shaped. A treatment source is mounted on the machine frame and can emit a treatment beam. Before the radiotherapy, a patient needs to be positioned by moving the treatment couch, so as to align the affected part of the patient with the beam focus of the treatment source.

In the related art, when positioning the patient, a locating head frame or a laser positioning system can be generally used. The position of the treatment couch can be adjusted according to a relationship between a coordinate system of the locating head frame or a center point of the laser positioning system and the beam focus of the treatment source, so as to align the affected part of the patient with the beam focus of the treatment source.

However, with the methods in the related art, the positioning accuracy depends on the locating head frame or the laser positioning system, and the positioning errors are large, which influences the effects of radiotherapy. In order to solve this problem, there are disclosed in some methods that the image system disposed on a floor and a ceiling is adopted for positioning. However, due to that the imaging system and the radiotherapy device are arranged separately, the locating accuracy of the radiotherapy device is low, and the installation and debugging process is complicated and long in cycle.

SUMMARY

There are provided in the present disclosure a radiotherapy device and a system.

In a first aspect, there is provided a radiotherapy device, comprising a fixed machine frame, a rotary machine frame, an imaging device and a treatment couch disposed on a side of the fixed machine frame, the treatment couch being capable of moving away from or close to the fixed machine frame along a first direction; wherein the rotary machine frame is rotatably connected to the fixed machine frame, and the rotary machine frame is provided with a treatment source, and the imaging device comprises a ray emitter and a detector which are disposed oppositely, the ray emitter and/or the detector are/is disposed on the fixed machine frame, and rays emitted by the ray emitter are received by the detector after passing an affected part of a patient, so as to capture images of the affected part of the patient.

Optionally, the ray emitter and/or the detector are/is capable of moving relative to the fixed machine frame, to move close to or away from the treatment couch.

Optionally, the device further comprises a support arm, wherein the support arm is connected with the ray emitter and/or the detector, the support arm drives the ray emitter and/or the detector connected thereto to move relative to the fixed machine frame, to move close to or away from the treatment couch; wherein the fixed machine frame comprises a machine frame main body and a base; and the support arm is disposed on the machine frame main body, or the support arm is disposed on the base.

Optionally, in a case of the support arm being disposed on the machine frame main body, the support arm drives the ray emitter and/or the detector connected thereto to move relative to the fixed machine frame via a slide rail; or the support arm drives the ray emitter and/or the detector connected thereto to move relative to the fixed machine frame via a rotary shaft; or the support arm is a telescopic arm.

Optionally, in a case of the support arm being disposed on the base, the support arm drives the ray emitter and/or the detector connected thereto to move relative to the fixed machine frame via a slide rail; or the support arm drives the ray emitter and/or the detector connected thereto to move relative to the fixed machine frame via a rotary shaft.

Optionally, the radiotherapy device comprises two groups of imaging devices and two support arms, and the two imaging devices are disposed on the two support arms respectively; and the two support arms are oppositely disposed on two sides of the fixed machine frame in a second direction, and the second direction is perpendicular to the first direction.

Optionally, an included angle of the rays emitted by the ray emitters in the two groups of imaging devices ranges from 60 degrees to 120 degrees.

In a second aspect, there is provided a radiotherapy system, comprising the radiotherapy device according to the aspect.

Optionally, the system further comprises a registration device establishing a communication connection with the radiotherapy device; wherein the radiotherapy device is configured to send the images of an affected part captured during positioning verification to the registration device; and the registration device is configured to determine positioning errors according to the images of the affected part and pre-stored diagnostic scan images of the affected part.

Optionally, the system further comprises: a positioning control device establishing a communication connection with the radiotherapy device and the registration device respectively; wherein the registration device is further configured to send the positioning errors to the positioning control device; and the positioning control device is configured to adjust the position of the treatment couch in the radiotherapy device according to the positioning errors.

There are provided in the present disclosure a radiotherapy device and a system. The radiotherapy device comprises the imaging device disposed on the fixed machine frame. The imaging device comprises the ray emitter and the detector which are disposed oppositely. The rays emitted by the ray emitter can be received by the detector after passing the affected part of the patient, so as to capture the images of the affected part of the patient. Since the imaging device and the radiotherapy device are integrally designed, the locating accuracy of the radiotherapy device is effectively improved, and the effects of radiotherapy are improved.

Meanwhile, at least one device (the ray emitter and/or the detector) in the imaging device is disposed on the fixed machine frame in the radiotherapy device, such that an engineer only needs to mount and debug one device in the imaging device at most in the process of mounting and debugging the radiotherapy device, thereby effectively reducing the time for mounting and debugging the imaging device In addition, the imaging device in the radiotherapy device provided in the embodiment of the present disclosure can move relative to the fixed machine frame to move close to or away from the treatment couch. When the imaging device works, the imaging device is moved into the working positions. When the imaging device stops working, the imaging device is moved out of the working positions, thereby avoiding the influence on the operation of the therapist.

It should be understood that both the foregoing general description and the following detailed description are merely exemplary and explanatory and are not intended to limit the present disclosure.

DETAILED DESCRIPTION

In order to make the principle and advantages of the present disclosure clearer, the embodiments of the present disclosure will be described in further detail in combination with the accompanying drawings.

At present, the radiotherapy device usually comprises a fixed machine frame, a rotary machine frame and a treatment couch. The fixed machine frame and the rotary machine frame are rotatably connected, and the fixed machine frame can support the rotary machine frame to rotate. The rotary machine frame is an annular, helmet-shaped or C-shaped structure having an opening in the center. The rotary machine frame is provided with a treatment source. The treatment couch is located on a side of the fixed machine frame, and configured to support a patient.

Figure 1:
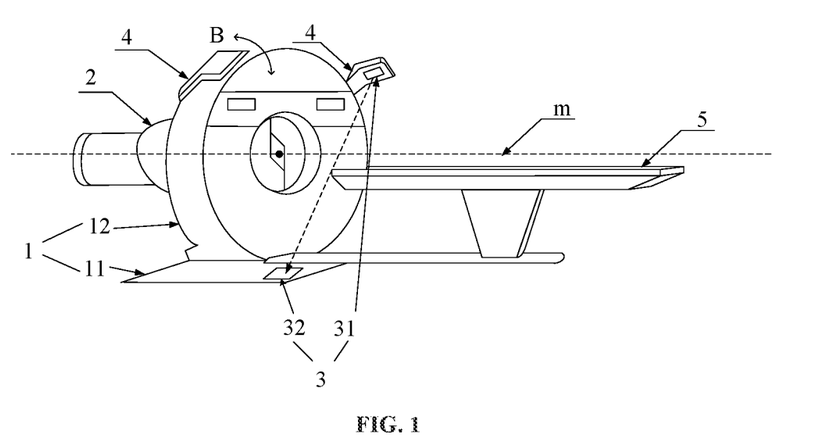
FIG. 1 is a schematic diagram of a structure of a radiotherapy device provided in an embodiment of the present disclosure.

FIG. 1 is a schematic diagram of a structure of a radiotherapy device provided in an embodiment of the present disclosure. As shown in FIG. 1, the radiotherapy device may comprise a fixed machine frame 1, a rotary machine frame 2 and a treatment couch 5 disposed on a side of the fixed machine frame 1. Herein, the rotary machine frame 2 is provided with a treatment source (not shown). The treatment couch 5 may be moved away from or close to the fixed machine frame 1 along a first direction. The first direction is the direction of an axis m of the fixed machine frame 1.

In the process of radiotherapy, the treatment source can be rotated around the body of the patient under driving of the rotary machine frame 2, and can treat an affected part of the patient from various angles. Besides, due to the arrangement of the rotary machine frame 2, the long time and consistent irradiation of rays emitted by the treatment source on non-affected parts (i.e., normal tissues and organs) of the patient can be avoided.

For the head radiotherapy devices, the fixed machine frame 1 may be annular, and the rotary machine frame 2 may be helmet-shaped with an opening in the center. For the body radiotherapy devices, the fixed machine frame 1 may be annular or rectangular, and the rotary machine frame 2 may be a roller or C-shaped arm. In the embodiments of the present disclosure, the head radiotherapy device with the fixed machine frame 1 being annular is taken as an example for explanation.

As shown in FIG. 1, the radiotherapy device according to the present disclosure further comprises an imaging device 3. The imaging device 3 may comprise a ray emitter 31 and a detector 32 which are disposed oppositely. The ray emitter 31 and/or the detector 32 are/is disposed on the fixed machine frame 1. The rays emitted by the ray emitter 31 are received by the detector 32 after passing the affected part of the patient, so as to capture images of the affected part of the patient.

The above ray emitter 31 may be an X ray tube. The treatment source may emit X-rays or gamma (γ) rays. Herein, the energy of the rays emitted by the treatment source is relatively high, generally in a megavolt level. The energy of the rays emitted by the ray emitter 31 is relatively low, generally in a kilovolt level.

Herein, the fixed machine frame 1 comprises a machine frame main body 12 and a base 11. Therefore, the ray emitter 31 and/or the detector 32 in the imaging device 3 may be disposed on the machine frame main body 12, and may also be disposed on the base 11.

In one aspect, the ray emitter 31 and the detector 32 in the imaging device 3 may be both disposed on the machine frame main body 12, or may also be both disposed on the base 11. In another aspect, one of the ray emitter 31 and the detector 32 in the imaging device 3 may be disposed on the machine frame main body 12 or the base 11, and the other one in the imaging device 3 may be symmetrically disposed on the ground or the ceiling in an intersecting manner with the longitudinal section of the axis m of the fixed machine frame 1 as a symmetric surface. For example, the devices in the imaging device 3 may be mounted on the ground of a treatment room directly. Alternatively, the devices in the imaging device 3 may also be mounted on the ceiling directly. It can be understood that one of the ray emitter 31 and the detector 32 in the imaging device 3 may be disposed on the machine frame main body 12, and the other one may be disposed on the base 11. For example, in the structure shown in FIG. 1, the ray emitter 31 is disposed on the machine frame main body 12, and the detector 32 is disposed in a position on the base 11 opposite to the ray emitter 31. The rays emitted by the ray emitter 31 are received by the detector 32 after passing the affected part of the patient, such that the imaging device 3 can realize the capture of the images of the affected part of the patient.

It should be noted that there may be one group or a plurality of groups of imaging devices 3. When the radiotherapy device only comprises one group of imaging device 3, the ray emitter 31 and the detector 32 in the imaging device 3 should be able to move. When the images of the affected part of the patient are captured, the ray emitter 31 and the detector 32 may be controlled to move simultaneously, to ensure that the one group of imaging device 3 can capture the images of the affected part from at least two different angles.

It also should be noted that if the radiotherapy device comprises a plurality of groups of imaging devices 3 at different angles, in the process of capturing the images of the affected part of the patient, the devices in the imaging devices 3 may not move, and the multiple groups of imaging devices 3 are directly adopted to obtain the images of the affected part at multiple different angles.

In the embodiments of the present disclosure, the imaging device 3 can capture the images of the affected part in the process of positioning verification, and send the images of the affected part to a registration device, so that the registration device can determine positioning errors according to the images of the affected part.

In conclusion, the radiotherapy device provided in the embodiments of the present disclosure comprises the imaging device disposed on the fixed machine frame. The imaging device comprises the ray emitter and the detector which are disposed oppositely. Herein, the rays emitted by the ray emitter can be received by the detector after passing the affected part of the patient, thereby capturing the images of the affected part of the patient. Since the imaging device and the radiotherapy device are integrally designed, the locating accuracy of the radiotherapy device can be effectively improved, and the effects of radiotherapy can be improved.

Meanwhile, at least one device (the ray emitter and/or the detector) in the imaging device is disposed on the fixed machine frame in the radiotherapy device, such that an engineer only needs to mount and debug one device in the imaging device at most in the process of mounting and debugging the radiotherapy device, thereby effectively reducing the time for mounting and debugging the imaging device.

In another embodiment of the present disclosure, the ray emitter 31 and/or the detector 32 in the imaging device 3 may be movably connected to the fixed machine frame 1, such that the ray emitter 31 and/or the detector 32 can move relative to the fixed machine frame 1, so as to get close to or move away from the treatment couch 5.

Exemplarily, the ray emitter 31 and/or the detector 32 may be directly connected to the fixed machine frame 1 via a slide rail, such that the ray emitter 31 and/or the detector 32 can move relative to the fixed machine frame 1, so as to get close to or move away from the treatment couch 5. That is, when the imaging device is required to capture the images of the affected part of the patient, the ray emitter 31 and/or the detector 32 may move along the slide rail from an initial position to get close to the treatment couch 5, so as to capture the images of the affected part of the patient. After the imaging device finishes working, the ray emitter 31 and/or the detector 32 may move along the slide rail to get away from the treatment couch 5 and return to the initial position.

Exemplarily, the ray emitter 31 and/or the detector 32 may be connected to the machine frame main body 12 via a support arm. The support arm drives the ray emitter 31 and/or the detector 32 to move relative to the machine frame main body 12, so as to get close to or move away from the treatment couch 5.

Figure 2:
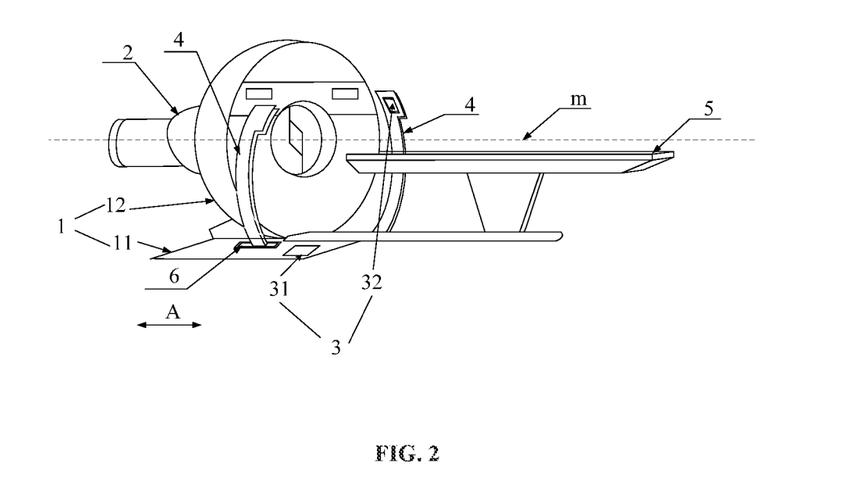
FIG. 2 is a schematic diagram of a structure of another radiotherapy device provided in an embodiment of the present disclosure.

With reference to FIGS. 1 and 2, the radiotherapy device may further comprise a support arm 4 on which the above-mentioned ray emitter 31 and/or the detector 32 may be connected. Herein, the support arm 4 is configured to drive the ray emitter 31 and/or the detector 32 connected thereto to move relative to the fixed machine frame 1, to get close to or move away from the treatment couch 5.

Herein, the support 4 may be disposed on the machine frame main body 12, and may also be disposed on the base 11.

In the case of the support arm 4 being disposed on the machine frame main body 12, in an optional implementation, one of the ray emitter 31 and the detector 32 in each group of imaging device 3 may be disposed on one support arm 4, and the other one in the ray emitter 31 and the detector 32 may be disposed on the base 11 or may be disposed on the floor or the ceiling of the treatment room.

Exemplarily, in the structure shown in FIG. 1, the two support arms 4 are disposed on one end, away from the base 11, of the machine frame main body 12. The ray emitter 31 is disposed on one end, away from the machine frame main body 12, of the support arm 4. The detector 32 is disposed on the base 11. The ray emitter 31 and the detector 32 in each group of imaging device 3 are disposed oppositely, that is, the rays emitted by the ray emitter 31 can be received by the detector 32 after passing the affected part of the patient.

In another optional implementation, the ray emitter 31 and the detector 32 in the imaging device 3 may be both disposed on the support arm 4. At this point, the two opposite positions of the machine frame main body 12 may be provided with one support arm 4 respectively. That is, in the imaging device 3, the ray emitter 31 may be disposed on one support arm 4, and the detector 32 may be disposed on the other support arm 4, thereby ensuring that the ray emitter 31 and the detector 32 are disposed oppositely. That is, the rays emitted by the ray emitter 31 can be received by the detector 32 after passing the affected part of the patient.

In the case of the support arms 4 being disposed on the base 11, in an optional implementation, one of the ray emitter 31 and the detector 32 in each group of imaging device 3 may be disposed on one end, away from the base 11, of one support arm 4, and the other one of the ray emitter 31 and the detector 32 may be disposed on the ground or the base 11, or may be disposed on one end, close to the base 11, of the other support arm 4 opposite to the one support arm 4.

In another optional implementation, one of the ray emitter 31 and the detector 32 in each group of imaging device 3 may be disposed on one end, close to the base 11, of one support arm 4, and the other one of the ray emitter 31 and the detector 32 may be disposed on the ceiling, or may be disposed on one end, away from the base 11, of the other support arm 4 opposite to the one support arm 4.

FIG. 2 is a schematic diagram of a structure of another radiotherapy device provided in an embodiment of the present disclosure. In the structure as shown in FIG. 2, the two support arms 4 are both disposed on the base 11. Herein, the detector 32 is disposed on one end, away from the base 11, of one support arm 4. The rail emitter 31 is disposed at a position, opposite to the detector, on the base 11. That is, the rays emitted by the ray emitter 31 can be received by the detector 32 after passing the affected part of the patient.

Figure 3:
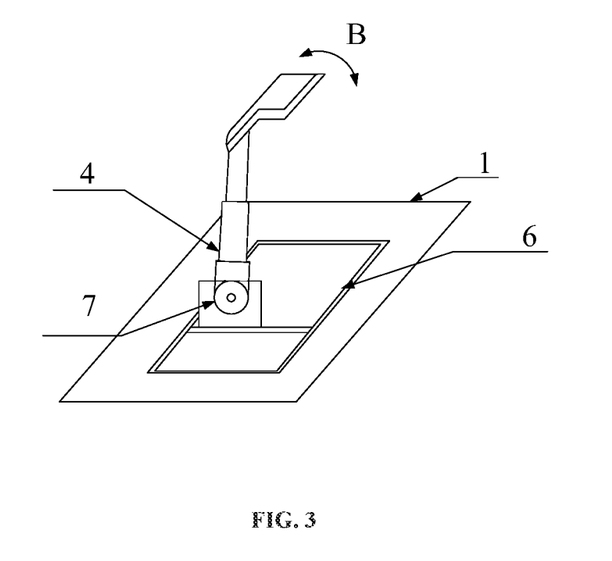
FIG. 3 shows a connection method between a support arm and a machine frame provided in an embodiment of the present disclosure.

In the case of the support arms 4 being disposed on the machine frame main body 12, optionally, as shown in FIG. 3, the support arms 4 may drive the ray emitter 31 and/or the detector 32 connected thereto to move relative to the fixed machine frame 1 via a slide rail 6. Alternatively, the support arms 4 may also drive the ray emitter 31 and/or the detector 32 connected thereto to move relative to the fixed machine frame 1 via a rotary shaft 7.

In one aspect, the machine frame main body 12 may be provided with the slide rail 6. Each support arm 4 may be connected to the machine frame main body 12 via the slide rail 6. Each support arm 4 may move along an extending direction of the slide rail 6, and further drive the ray emitter 31 and/or the detector 32 to move away from or close to the treatment couch 5 along the slide rail 6.

In another aspect, each support arm 4 may also be connected to the machine frame main body 12 via the rotary shaft 7. Each support arm 4 can rotate along a direction close to or away from the treatment couch 5.

Further, when the support arms 4 are disposed on the machine frame main body 12, each support arm 4 may also be a telescopic arm. As shown in FIG. 3, the length of the telescopic arms is adjustable. The ray emitter 31 and/or the detector 32 may be driven by the telescopic arms to move close to or get away from the treatment couch 5. Therefore, when the imaging device is not used, in order to avoid the influence on the operation of a therapist, the lengths of the support arms 4 may be adjusted in addition to the moving and rotating of the support arms 4, thereby further improving the flexibility during use of the radiotherapy device.

When the support arms 4 are disposed on the base, optionally, as shown in FIG. 2, the support arms 4 may drive the ray emitter 31 and/or the detector 32 connected thereto to move relative to the fixed machine frame 1 via the slide rail 6. Alternatively, the support arms 4 may also drive the ray emitter 31 and/or the detector 32 connected thereto to move relative to the fixed machine frame 1 via the rotary shaft 7.

In one aspect, the base 11 may be provided with the slide rail 6. Each support arm 4 may be connected to the base 11 via the slide rail 6. The support arm 4 may move along an extending direction of the slide rail 6, and further drive the ray emitter 31 and/or the detector 32 to move away from or close to the treatment couch 2 along the extending direction of the slide rail 6. The extending direction of the slide rail 6 may be consistent with a direction of an axis m of the fixed machine frame 1, i.e., the direction A in FIG. 2. Alternatively, the extending direction of the slide rail 6 may be perpendicular to the direction of the axis m of the fixed machine frame 1.

In another aspect, the base 11 may be provided with the rotary shaft 7. Each support arm 4 may also be connected to the base 11 via the rotary shaft 7. At this point, each support arm 4 may rotate along a direction close to the away from the treatment couch 5 via the rotary shaft 7, i.e., the direction B as shown in FIGS. 2 and 3. A rotary direction of the rotary shaft may be consistent with a direction of an axis m of the fixed machine frame, and may also be perpendicular to the direction of the axis m of the fixed machine frame.

It should be noted that in the embodiments of the present disclosure, a sliding part may also be disposed in the slide rail 6 disposed on the machine frame main body 12 or the base 11. Each support arm 4 may be connected to the sliding part via the rotary shaft 7. Therefore, each support arm 4 not only can slide along the extending direction of the slide rail 6, but also can rotate, thereby effectively improving the flexibility of the support arms 4 during use.

It also should be noted that when the support arms 4 are disposed on the base 11, the shape of each support arm 4 may be adapted to the shape of the machine frame main body 12. For example, as shown in FIG. 2, the shape of the machine frame main body 12 is annular, and then the support arms 4 may be arc-shaped. In addition, the support arms 4 may also be the support arms in other shapes. The specific shapes of the support arms are not limited in the embodiments of the present disclosure.

Optionally, in order to ensure the accuracy of the captured images of the affected part, a plurality of groups of imaging devices 3 may be disposed in the radiotherapy device. The more the number of groups of the imaging devices 3 is, the higher the accuracy of the captured images of the affected part is, the better the positioning effect is, but the higher the cost is. Therefore, in order to save the cost on the basis of ensuring the positioning effect, in the embodiments of the present disclosure, as shown in FIG. 2, two groups of imaging devices 3 and two support arms 4 may be disposed in the radiotherapy device. The devices in the two groups of imaging devices 3 may be disposed on the two support arms 4 respectively. The two support arms 4 may be oppositely disposed on the base 11 on both sides of the fixed machine frame 1 in a second direction, and the second direction is perpendicular to the first direction. That is, the second direction is perpendicular to the direction of the axis m of the fixed machine frame 1. In other words, the two ray emitters 31 of the two groups of imaging devices 3 are located on the ends, away from the base 11, of the two support arms 4 respectively. The two detectors 32 are located on the ends, close to the base 11, of the two support arms 4 respectively. The two groups of imaging devices are disposed in an intersecting manner. Alternatively, the ray emitters 31 of the two groups of imaging devices 3 are located on the ends, away from the base 11 and close to the base 11, of one support arm 4 respectively. The two detectors 32 are located on the ends, close to the base 11 and away from the base 11, of the other support arm 4 respectively. The two groups of imaging devices are disposed in an intersecting manner.

Further, as shown in FIG. 2, the two groups of imaging devices 3 are symmetrically disposed in a mirror-image intersecting manner with the longitudinal section of the axis m of the fixed machine frame 1 as a symmetric surface. The included angle α of the rays emitted by the ray emitters 31 in the two groups of imaging devices 3 may be 60 degrees to 120 degrees, and for example, may be 90 degrees.

Further, the radiotherapy device provided in the embodiments of the present disclosure may further comprise a driving device (not shown). The driving device may be electrically connected to the imaging device 3 or each support arm 4, and configured to drive the imaging device 3 or each support arm 4 to move. Correspondingly, a driving switch may also be disposed in the radiotherapy device. When the driving switch is triggered (for example, triggered by pressing or rotating), the driving device begins to work, and drives the imaging device 3 or each support arm 4 to move, such that certain device of the imaging device 3 moves to or away from working positions.

In the embodiments of the present disclosure, the therapist may control the driving device to control the imaging device 3 or each support arm 4 to move, such that the devices in the imaging device 3 move to or away from the working positions. The working positions may comprise positioning working positions. The positioning working positions are the positions at which the devices in each group of imaging device 3 are located during positioning verification. When the devices in each group of imaging device 3 are in the working positions, the rays emitted by the ray emitter 31 in the imaging device 3 can pass by the affected part of the patient during positioning and can be received by the detector 32. The working positions are fixed positions predetermined when the radiotherapy device is produced and are not required to be set by the therapist.

Further, the working positions may further comprise treatment working positions. In the embodiments of the present disclosure, in order to improve the accuracy of the radiotherapy, the affected part of the patient is monitored in real time when the radiotherapy is performed on the patient. Then the devices in each group of imaging device 3 may be located in the treatment working positions in the treatment process. At this point, the rays emitted by the ray emitter 31 in the imaging device 3 can pass by the affected part of the patient during treatment and can be received by the detector 32.

In the process of radiotherapy, before the imaging devices 3 is adopted to perform positioning on the patient, the therapist still needs to adjust a body position of the patient, locate the patient and the like. In order to avoid the influence of the imaging devices 3 or the support arms 4 on the operation of the therapist, the imaging devices 3 or the support arms 4 may be moved to cause the devices in the imaging devices 3 to get away from the positioning working positions and the treatment working positions. After the therapist finishes the operations required before the positioning, the imaging devices 3 or the support arms 4 may be moved again, so as to move the devices in the imaging devices 3 to the positioning working positions. Afterwards, the imaging devices 3 may be adopted to perform positioning on the patient.

When the imaging devices 3 are used for positioning, the therapist may firstly adjust the position of the treatment couch 5 according to experience, such that the affected part of the patient is located nearby an inlet of the rotary machine frame 2. Afterwards, the imaging devices 3 can be switched on. At this point, each ray emitter 31 in the imaging devices 3 emits X-rays. The X-rays are attenuated to different extents when being transmitted through the objects having different thicknesses, while the thicknesses of different tissues or organs in a human body are different. Therefore, the X-rays will be attenuated to different extents when passing an area of the affected part. After the detector 32 receives the attenuated X-rays, the corresponding images of the affected part are generated and sent to the registration device. Diagnostic scan images of the affected part of the patient are pre-stored by the registration device. The registration device may perform registration on the images of the affected part and the diagnostic scan images of the affected part to determine the positioning errors. Afterwards, the position of the treatment couch can be accurately adjusted according to the positioning errors.

After the positioning is finished, the imaging device 3 or the support arm 4 may be moved, such that the devices in the imaging devices 3 can get away from the positioning working positions and then move to the treatment working positions. Therefore, the affected part of the patient can be tracked in real time in the therapy process.

In conclusion, the radiotherapy device provided in the embodiments of the present disclosure comprises the imaging device disposed on the fixed machine frame. The imaging device comprises the ray emitter and the detector which are disposed oppositely. Herein, the rays emitted by the ray emitter can be received by the detector after passing the affected part of the patient, thereby capturing the images of the affected part of the patient. Since the imaging device and the radiotherapy device are integrally designed, the locating accuracy of the radiotherapy device can be effectively improved, and the effects of radiotherapy can be improved.

Meanwhile, at least one device (the ray emitter and/or the detector) in the imaging device is disposed on the fixed machine frame in the radiotherapy device. Therefore, in the process of mounting and debugging the radiotherapy device, the engineer only needs to mount and debug one device in the imaging device at most, thereby effectively reducing the time for mounting and debugging the imaging device.

In addition, the imaging device in the radiotherapy device provided in the embodiment of the present disclosure can move relative to the fixed machine frame to get close to or move away from the treatment couch. When the imaging device works, the imaging device is moved into the working positions. When the imaging device stops working, the imaging device is moved out of the working positions, thereby avoiding the influence on the operation of the therapist.

There is provided in the embodiment of the present disclosure a radiotherapy system. The radiotherapy system may comprise the radiotherapy device according to any one of FIGS. 1 to 3.

Figure 4:
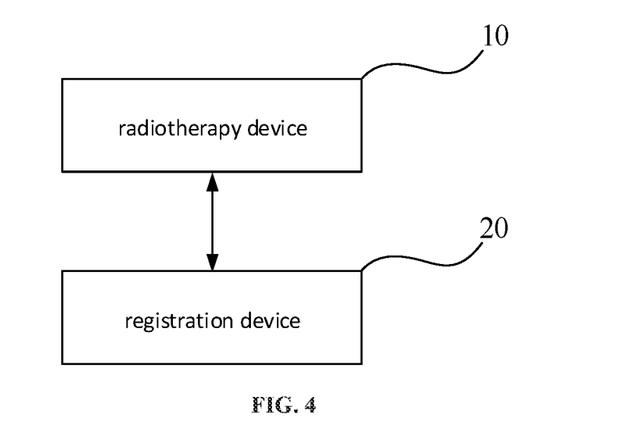
FIG. 4 is a schematic diagram of a radiotherapy system provided in an embodiment of the present disclosure.

FIG. 4 is a schematic diagram of the radiotherapy system provided in the embodiments of the present disclosure. As shown in FIG. 4, the radiotherapy system may further comprise a registration device 20 establishing a communication connection with the radiotherapy device 10.

The radiotherapy device 10 is configured to send the captured images of the affected part to the registration device 20.

The registration device 20 is configured to determine positioning errors of the affected part according to the images of the affected part and pre-stored diagnostic scan images of the affected part.

The diagnostic scan images of the affected part pre-stored in the registration device 20 are three-dimensional images. The images of the affected part captured by the imaging device are two-dimensional images. In order to perform registration on the diagnostic scan images of the affected part and the images of the affected part, the registration device 20 firstly needs to convert the three-dimensional diagnostic scan images of the affected part to two-dimensional diagnostic scan images of the affected part by using a digitally reconstructed radiograph (DRR) technology, and further registers the images of the affected part with the two-dimensional diagnostic scan images of the affected part, so as to determine the positioning errors of the affected part.

Figure 5:
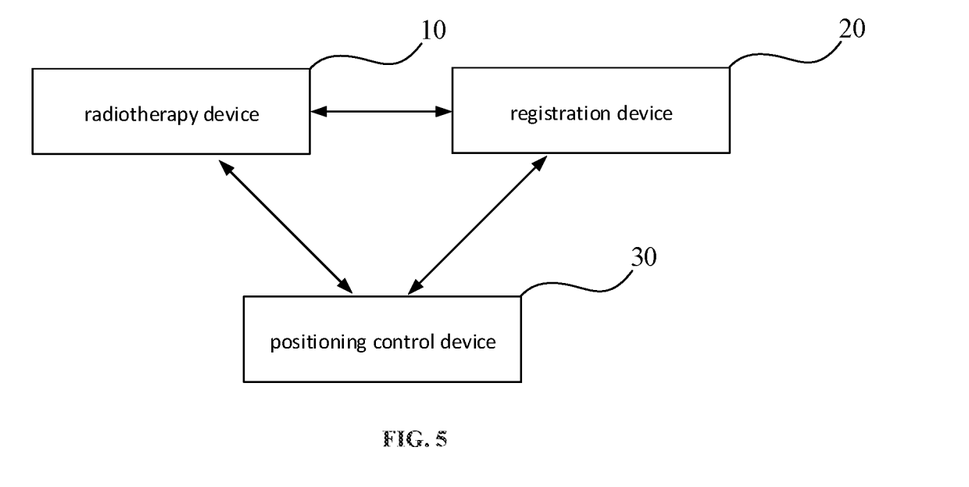
FIG. 5 is a schematic diagram of another radiotherapy system provided in an embodiment of the present disclosure.

FIG. 5 is a schematic diagram of another radiotherapy system provided in the embodiments of the present disclosure. As shown in FIG. 5, the system may also comprise a positioning control device 30 establishing a communication connection with the radiotherapy device 10 and the registration device 20 respectively.

Herein, the registration device 20 is further configured to send positioning errors to the positioning control device 30.

The positioning control device 30 is configured to adjust the position of the treatment couch 2 in the radiotherapy device 10 according to the positioning errors, thereby realizing the synergetic work of the radiotherapy device, the registration device and the positioning control device, and improving the efficiency of radiotherapy effectively.

In conclusion, the radiotherapy system provided in the embodiments of the present disclosure comprises the radiotherapy device and the registration device. The radiotherapy device comprises the imaging device. The imaging device comprises the ray emitter and the detector which are disposed oppositely. Herein, the rays emitted by the ray emitter can be received by the detector after passing through the affected part of the patent. During the positioning verification, the imaging device can capture the images of the affected part of the patient, and sends the images of the affected part to the registration device. The registration device determines the positioning errors according to the images of the affected part. Afterwards, the position of the treatment couch can be accurately adjusted by the positioning control device according to the positioning errors, which effectively improves the positioning accuracy and improves the effects of radiotherapy.

The foregoing is merely exemplary embodiments of the present disclosure and is not intended to limit the present disclosure. Any modifications, equivalent substitutions, improvements and the like made within the spirit and principle of the present disclosure shall fall into the protective scope of the appended claims of the present disclosure.

What is claimed is:

1. A radiotherapy device, comprising a fixed machine frame, a rotary machine frame, an imaging device and a treatment couch disposed on a side of the fixed machine frame, the treatment couch being capable of performing one of moving away from and moving close to the fixed machine frame along a first direction;
   wherein the rotary machine frame is rotatably connected to the fixed machine frame, and the rotary machine frame is provided with a treatment source; and
   the imaging device comprises a ray emitter and a detector which are disposed oppositely, at least one of the ray emitter and the detector is disposed on the fixed machine frame, and rays emitted by the ray emitter are received by the detector after passing an affected part of a patient, so as to capture images of the affected part of the patient.

2. The device according to claim 1, wherein at least one of the ray emitter and the detector is capable of moving relative to the fixed machine frame, to perform one of moving close to and moving away from the treatment couch.

3. The device according to claim 2, further comprising a support arm, wherein the support arm is connected with at least one of the ray emitter and the detector, the support arm drives at least one of the ray emitter and the detector connected thereto to move relative to the fixed machine frame, to perform one of moving close to away from the treatment couch;
   wherein the fixed machine frame comprises a machine frame main body and a base; and the support arm is disposed on one of the machine frame main body and the base.

4. The device according to claim 3, wherein in a case of the support arm being disposed on the machine frame main body, the support arm drives at least one of the ray emitter and the detector connected thereto to move relative to the fixed machine frame via a slide rail.

5. The device according to claim 3, wherein in a case of the support arm being disposed on the base, the support arm drives at least one of the ray emitter and the detector connected thereto to move relative to the fixed machine frame via a slide rail.

6. The device according to claim 5, wherein the radiotherapy device comprises two groups of imaging devices and two support arms, and the two imaging devices are disposed on the two support arms respectively; and
   the two support arms are oppositely disposed on two sides of the fixed machine frame in a second direction, and the second direction is perpendicular to the first direction.

7. The device according to claim 6, wherein an included angle of the rays emitted by the ray emitters in the two groups of imaging devices ranges from 60 degrees to 120 degrees.

8. The device according to claim 3, wherein in a case of the support arm being disposed on the machine frame main body, the support arm drives at least one of the ray emitter and the detector connected thereto to move relative to the fixed machine frame via a rotary shaft.

9. The device according to claim 3, wherein in a case of the support arm being disposed on the machine frame main body, the support arm is a telescopic arm.

10. The device according to claim 3, wherein in a case of the support arm being disposed on the base, the support arm drives at least one of the ray emitter and the detector connected thereto to move relative to the fixed machine frame via a rotary shaft.

11. The method according to claim 2, wherein at least one of the ray emitter and the detector is capable of moving relative to the fixed machine frame, to perform one of moving close to and moving away from the treatment couch along a direction parallel to the first direction.

12. A radiotherapy system, comprising a radiotherapy device comprising a fixed machine frame, a rotary machine frame, an imaging device and a treatment couch disposed on a side of the fixed machine frame, the treatment couch being capable of performing one of moving away from and moving close to the fixed machine frame along a first direction;
   wherein the rotary machine frame is rotatably connected to the fixed machine frame, and the rotary machine frame is provided with a treatment source; and
   the imaging device comprises a ray emitter and a detector which are disposed oppositely, at least one of the ray emitter and the detector is disposed on the fixed machine frame, and rays emitted by the ray emitter are received by the detector after passing an affected part of a patient, so as to capture images of the affected part of the patient.

13. The system according to claim 12, further comprising a registration device establishing a communication connection with the radiotherapy device;
   wherein the radiotherapy device is configured to send the images of an affected part captured during positioning verification to the registration device; and
   the registration device is configured to determine positioning errors according to the images of the affected part and pre-stored diagnostic scan images of the affected part.

14. The system according to claim 13, further comprising: a positioning control device establishing a communication connection with the radiotherapy device and the registration device respectively;
   wherein the registration device is further configured to send the positioning errors to the positioning control device; and
   the positioning control device is configured to adjust the position of the treatment couch in the radiotherapy device according to the positioning errors.

15. The system according to claim 12, wherein at least one of the ray emitter and the detector is capable of moving relative to the fixed machine frame, to perform one of moving close to and moving away from the treatment couch.

16. The system according to claim 15, further comprising a support arm, wherein the support arm is connected with at least one of the ray emitter and the detector, the support arm drives at least one of the ray emitter and the detector connected thereto to move relative to the fixed machine frame, to perform one of moving close to and moving away from the treatment couch:
   wherein the fixed machine frame comprises a machine frame main body and a base; and the support arm is disposed on one of the machine frame main body and the base.

17. The system according to claim 16, wherein in a case of the support arm being disposed on the machine frame main body, the support arm drives at least one of the ray emitter and the detector connected thereto to move relative to the fixed machine frame via a slide rail.

18. The system according to claim 16, wherein in a case of the support arm being disposed on the base; the support arm drives at least one of the ray emitter and the detector connected thereto to move relative to the fixed machine frame via a slide rail.

19. The system according to claim 18, wherein the radiotherapy device comprises two groups of imaging devices and two support arms, and the two imaging devices are disposed on the two support arms respectively; and the two support arms are oppositely disposed on two sides of the fixed machine frame in a second direction, and the second direction is perpendicular to the first direction.

20. The system according to claim 19, wherein an included angle of the rays emitted by the ray emitters in the two groups of imaging devices ranges from 60 degrees to 120 degrees.

* * * * *